ves Patent [19]

United States Patent [19]
Morisawa et al.

[11] 3,983,238
[45] Sept. 28, 1976

[54] SUBSTITUTED PYRIDINOL-CONTAINING COMPOSITIONS AND METHODS FOR THE TREATMENT OF COCCIDIOSIS

[75] Inventors: Yasuhiro Morisawa; Mitsuru Kataoka; Taiichiro Watanabe; Noritoshi Kitano; Toshiaki Matsuzawa, all of Tokyo, Japan

[73] Assignee: Sankyo Company Limited, Tokyo, Japan

[22] Filed: Mar. 12, 1975

[21] Appl. No.: 557,522

Related U.S. Application Data

[60] Continuation-in-part of Ser. No. 509,721, Sept. 26, 1974, abandoned, which is a division of Ser. No. 404,641, Oct. 9, 1973, Pat. No. 3,897,556.

[30] Foreign Application Priority Data

Oct. 20, 1972  Japan............................. 47-105090
Apr. 11, 1973  Japan............................. 48-41111

[52] U.S. Cl................................. 424/266; 424/263
[51] Int. Cl.²............................................ A61K 31/44
[58] Field of Search............................ 424/263, 266

[56] References Cited
UNITED STATES PATENTS 3,644,385  2/1972  Utsumi et al. ..................... 424/266

Primary Examiner—Frederick E. Waddell
Attorney, Agent, or Firm—Flynn & Frishauf

[57] ABSTRACT

An anticoccidial composition which comprises a compound of the formula

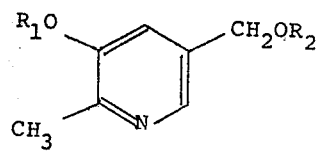

intimately dispersed in an inert edible carrier, wherein $R_1$ and $R_2$ are each hydrogen, an aliphatic acyl group, an aromatic acyl group or a heterocyclic acyl group, and at least $R_1$ and $R_2$ is said heterocyclic acyl group; or a salt thereof.

The composition is a preventive and curative anticoccidial agent for poultry and domestic animals. Particularly, it shows a significant activity against chronic coccidiosis caused by *Eimeria acervulina*.

The composition is less toxic for animals, besides it has an advantage that it is also effective for coccidiosis caused by coccidia resistant to the known anticoccidial agents.

66 Claims, No Drawings

SUBSTITUTED PYRIDINOL-CONTAINING COMPOSITIONS AND METHODS FOR THE TREATMENT OF COCCIDIOSIS

CROSS-REFERENCE TO RELATED APPLICATIONS

This is a Continuation-in-Part of Ser. No. 509,721 filed Sept. 26, 1974 which has been abandoned which was a Division of Ser. No. 404,641 filed Oct. 9, 1973, now U.S. Pat. No. 3,897,556.

This invention relates to novel compositions and methods for the treatment and prevention of the poultry disease coccidiosis.

More particularly, it is concerned with novel compositions containing, as an active anticoccidial agent, certain pyridinol derivatives.

Coccidiosis is a common and widespread disease of poultry, especially chickens and turkeys, and domestic animals such as rabbits, goats, sheep, and cattles, which disease is caused by a kind of protozoa belonging to class Sporozoa, order Coccidia, family Eimeriidae.

Coccidiosis of poultry and domestic animals is caused mainly by the protozoa belonging to genus Eimeria, which disease is classified to an acute type and a chronic one.

The former is caused by such species as E. tenella and E. necatrix, and the characteristic feature of the disease is a copious bloody discharges from the ceca and small intestine of diseased poultry, which often die within a day or two.

The latter is caused by such species of E. acervulina, E. maxima, E. brunetti, E. praecox, E. hagani, E. mitis and E. mivati, and the characteristic feature of the disease is that the mortality of diseased poultry is rather few, whereas a poor weight gain, a reduced feed efficiency and a reduced efficiency of egg-production are commonly observed.

In fact rabbits as well as cattles, sheep and goats sometimes have severe lesions caused by parasite Eimeria within their livers and intestines.

Oocysts of coccidia are excreted from an infected animal with feces, and spores having infectivity are produced within 24 – 48 hours under suitable conditions, which spores enter into a non-infected animal orally.

Oocysts grow at first asexually within the cells of the caecum or small intestine of the host animal, during which time the heaviest sympton is observed. Then, they grow sexually and are excreted with the feces of the host animal and they exhibit an awful communicability.

The elimination of control of coccidiosis is, therefore, of paramount importance particularly in the poultry industry.

There have been proposed many preventive and curative methods for coccidiosis. One of them is a development in chemotherapeutic agents such as sulfa drugs, arsenic compounds, nitrofuran derivatives, nitrophenide, Nicarbazine, Zoalane, pyrimidine derivatives (antithiamines), quinoline derivatives, quanidine derivatives, various antibiotics and so on.

But they have some defects; i.e. weak activity, narrow anti-protozoal spectrum, lack of security for animals or acquired resistance to the drugs by protozoa, respectively. Therefore, treatment with the hither-to-known anticoccidial agents are not satisfactory.

It is an object of this invention to provide novel compositions which are effective in treating and preventing coccidiosis.

Other objects will become apparent from the following detailed description of this invention.

In accordance with this invention, it has now been found that the pyridinol derivatives having the formula

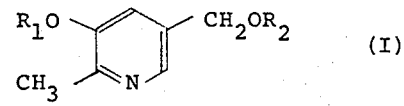

intimately dispersed in an inert edible carrier, wherein $R_1$ and $R_2$ are each hydrogen, an aliphatic acyl group, an aromatic acyl group or a heterocyclic acyl group, and at least $R_1$ or $R_2$ is said heterocyclic acyl group; or a salt thereof possess significant anticoccidial activity, and may be used in the methods and compositions of this invention.

The above compounds of formula (I) have a preventive and curative anticoccidial activity against almost all species of genus Eimeria especially against E. acervulina, to which no practically effective anticoccidial agents have been known.

In addition, some of the above compounds have a growth promoting activity for poultry and domestic animals and their preventive application to non-infected animals brings the promotion of weight gain and the improvement of feed efficiency.

With regard to the above formula (I), the aliphatic acyl group may be preferably a straight or branched alkanoyl or alkenoyl group of 2 to 18 carbon atoms in total, and the aliphatic acyl group may have substituents such as an aryloxy group, and the aliphatic acyl group may be cycloalkanoyl group of 6 to 8 carbon atoms in total, and exemplified by acetyl, propionyl, butyryl, valeroyl, hexanoyl, octanoyl, palmitoyl, stearoyl, isobutyryl, isovaleroyl, pivaloyl, crotonoyl, phenoxyacetyl, 2-phenoxypropionyl or cyclohexanecarbonyl; the aromatic acyl group may be preferably a benzoyl or a naphthoyl group which may have 1 to 2 substituents such as lower alkyl-, alkoxy-, halogen, nitro-, cyano-, carboxy- or acetylamino- in the aromatic ring and exemplified by benzoyl, naphthoyl, toluoyl, chlorobenzoyl, bromobenzoyl, methoxybenzoyl, nitrobenzoyl, cyanbenzoyl, carboxybenzoyl, acetylaminobenzoyl, 3,5-dimethylbenzoyl, 2,3-dimethoxybenzoyl or 3,4-dimethoxybenzoyl group; the heterocyclic acyl group is exemplified by 2-furoyl, 2-thenoyl, isonicotinoyl or nicotinoyl group.

In view of anticoccidial activity, preferred are the following pyridinol derivatives:

A compound in which $R_1$ is a hydrogen atom and $R_2$ is a furoyl group, a thenoyl group, a nicotinoyl group or an isonicotinoyl group; a compound in which $R_1$ is a furoyl group, a thenoyl group, a nicotinoyl group or an isonicotinoyl group and $R_2$ is hydrogen atom and; and a compound in which both $R_1$ and $R_2$ may be the same or different and each represents a furoyl group, a thenoyl group, a nicotinoyl group or an isonicotinoyl group.

More preferred are the following pyridinol derivatives:

A compound in which $R_1$ is a hydrogen atom and $R_2$ is a nicotinoyl group, an isonicotinoyl group, a furoyl group or a thenoyl group; a compound in which $R_1$ is a nicotinoyl group, an isonicitinoyl group, a furoyl group or a thenoyl group and $R_2$ is a hydrogen atom; a compound in which both $R_1$ and $R_2$ are the same and each represents a nicitinoyl group, an isonicotinoyl group, a furoyl group or a thenoyl group.

The acid adduct salts of the above formula (I) also possess anticoccidial activity.

There is no limitation to the acid so far as salts formed are pharmaceutically acceptable and nontoxic to animals.

Suitable salts of this invention are as follows: acid adduct salts in which an acid is an inorganic acid such as hydrochloric acid, sulfuric acid, nitric acid of phosphoric acid; an organic acid such as acetic acid, propionic acid, lactic acid, oxalic acid, succinic acid, maleic acid, tartaric acid, citric acid, benzoic acid, phthalic acid, terephthalic acid, naphthalene disulfonic acid.

The most preferable group of the pyridinol derivatives of the above formula (I) may include the following compound:
5-hydroxymethyl-2-methyl-3-(2-thenoyloxy)pyridine,
5-hydroxymethyl-2-methyl-3-nicotinoyloxypyridine,
3-isonicotinoyloxy-5-hydroxymethyl-2-methylpyridine and
3-(2-furoyloxy)-5-hydroxymethyl-2-methylpyridine.

The "Compound No." as given in the foregoing will be hereinafter frequently referred to.

The above illustrated compounds are all new compounds and readily prepared according to the process described below.

A. Process for the preparation of 3-mono ester derivatives of 5-hydroxymethyl-3-pyridinol

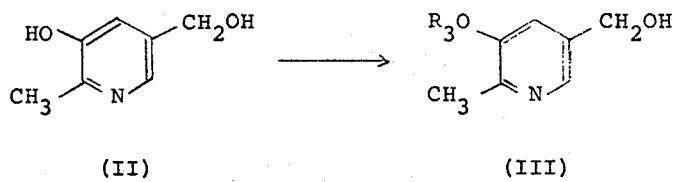

Of the pyridinol derivatives of the above formula (I), representative examples thereof are listed below, but they are not intended to limit the scope of this invention.

| Compound No. | Chemical Name |
|---|---|
| 1 | 5-hydroxymethyl-2-methyl-3-(2-thenoyloxy)-pyridine |
| 2 | 5-hydroxymethyl-2-methyl-3-nicotinoyloxy-pyridine |
| 3 | 5-(2-furoyloxymethyl)-2-methyl-3-pyridinol |
| 4 | 2-methyl-5-nicotinoyloxymethyl-3-pyridinol |
| 5 | 3-acetoxy-5-(2-furoyloxymethyl)-2-methyl-pyridine |
| 6 | 3-(2-furoyloxy)-5-(2-furoyloxymethyl)-2-methylpyridine |
| 7 | 2-methyl-3-nicotinoyloxy-5-nicotinoyloxy-methylpyridine |
| 8 | 3-benzoyloxy-5-(2-furoyloxymethyl)-2-methyl-pyridine |
| 9 | 3-(2-thenoyloxy)-5-(2-thenoyloxymethyl-2-methylpyridine |
| 10 | 5-isonicotinoyloxymethyl-3-methyl-3-pyridinol |
| 11 | 5-hydroxymethyl-3-isonicotinoyl-2-methyl-pydidine |
| 12 | 3-(2-furoyloxy)-5-hydroxymethyl-2-methyl-pyridine |
| 13 | 2-methyl-5-(2-thenoyloxymethyl)-3-pyridinol |
| 14 | 3-acetoxy-5-(2-thenoyloxymethyl)-2-methyl-pyridine |
| 15 | 3-acetoxy-2-methyl-5-nicotinoyloxymethyl-pyridine |
| 16 | 3-acetoxy-5-isonicotinoyloxymethyl-2-methylpyridine |
| 17 | 3-isonicitinoyloxy-5-isonicotinoyloxymethyl-2-methylpyridine | wherein $R_3$ is an aliphatic, an aromatic or a heterocyclic acyl group.

$A_1$. Method which includes an acid anhydride and water

5-Hydroxymethyl-2-methyl-3-pyridinol (II) or the salt thereof is dissolved in water. In case the salt is used, the solution is neutralized with an equilmoar alkali or a tertiary amine.

The reaction is performed by the addition of a saturated or unsaturated aliphatic carboxylic anhydride of 2 to 8 carbon atoms to the solution to form the compounds of formula (III).

$A_2$. Method which includes an acid halide, an amine and an organic solvent

5-Hydroxymethyl-2-methyl-3-pyridinol (II) or the salt thereof is dissolved or suspended in an aprotic solvent.

The reaction is performed by the addition of an equimolar aliphatic, aromatic or heterocyclic carboxylic halide to the solution in the presence of a tertiary amine under cooling to form the compounds of formula (III).

$A_3$. Method which includes an acid halide and water

To a solution of 5-hydroxymethyl-2-methyl-3-pyridinol (II) or the salt thereof is added an equimolar alkali or a tertiary amine. In case a salt is used, the addition of 2 molar alkali or tertiary amine is necessary for neutralization.

The reaction is performed by the addition of an equimolar aliphatic, aromatic or hetercyclic carboxylic halide to the solution to form the compounds of formula (III).

According to the above process (A), compounds Nos. 1, 11 and 12 are obtained.

B. Process for the preparation of 5-mono-ester derivatives of 5-hydroxymethyl-2-methyl-3-pyridinol

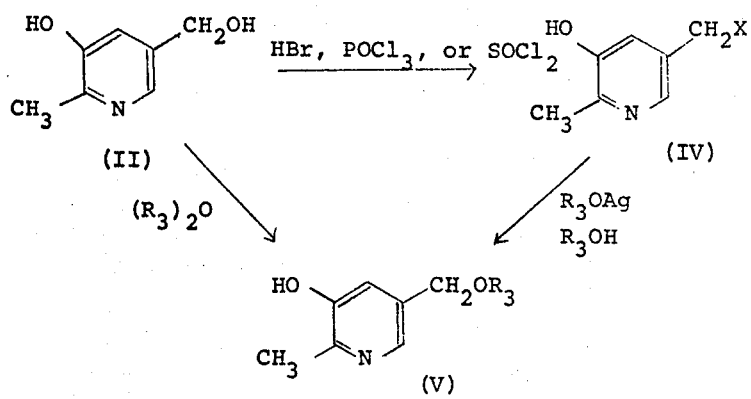

wherein $R_3$ has the same meaning as described in paragraph (A); X is a halogen atom.

$B_1$. Method which includes 5-halomethyl-2-methyl-3-pyridinol and a silver salt or an organic acid.

5-Hydroxymethyl-2-methyl-3-pyridinol (II) or the salt thereof is heated with hydrobromic acid, phosphorus oxychloride or thinoyl chloride to form 5-halomethyl-2-methyl-3-pyridinol (IV). The compound (IV) thus obtained is reacted with a silver salt of an organic acid in the corresponding organic acid to form the compounds of formula (V).

$B_2$. Method which includes an acid anhydride, an amine and an organic solvent

5-Hydroxymethyl-2-methyl-3-pyridinol or the salt thereof is reacted under heating with an equimolar aliphatic, aromatic or heterocyclic carboxylic anhydride in an aprotic solvent in the presence of pyridine or a tertiary amine to form the compounds of formula (V).

The method is suitable for obtaining 5-mono-ester derivatives in one step in good yield.

$B_3$. Method by the selective hydrolysis of 3,5-diesters of 5-hydroxymethyl-2-methyl-3-pyridinol

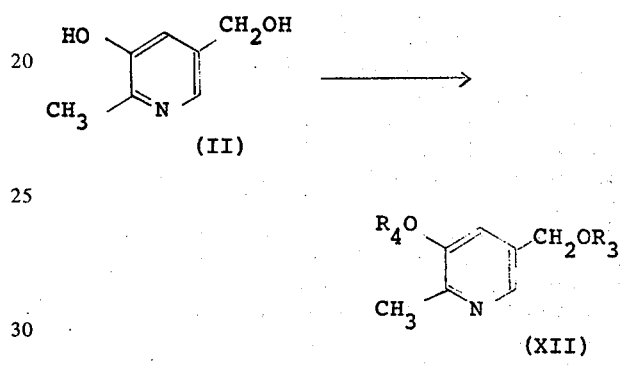

wherein $R_3$ and $R_4$, may be the same or different, are aliphatic, aromatic or heterocyclic acyl group.

The 3,5-Diesters of 5-hydroxymethyl-2-methyl-3-pyridinol or the salts thereof are selectively hydrolyzed in the presence of an acid to form the compounds of formula (V).

According to the above process (B), compounds Nos. 3, 4, 10 and 13 are obtained.

C. Process for the preparation of 3,5-disubstituted 5-hydroxymethyl-3-methyl-3-pyridinols (diester derivatives having the same substituents on 3- and 5-position)

wherein $R_3$ and $R_4$ have the same meaning as described above, respectively.

3,5-Diester derivatives of 5-hydroxymethyl-2-methyl-3-pyridinol having the same substituents on 3- and 5-position are obtained according to the aforementioned process (A) or (B) by using 2 molar or more corresponding reactions.

According to the above process (C), compounds Nos. 6, 7 and 9 are obtained.

D. Process for the preparation of 3,5disubstituted 5-hydroxymethyl-2-methyl-3-pyridinols (diesters having the different subsituents each other on 3- and 5-position)

Such compounds are obtained by optional combination of the processes for the preparation of the 3- or 5-substituted derivatives described in (A) or (B).

According to the above process (D), compound No. 5 is obtained.

REFERENTIAL EXAMPLE 1

5-Hydroxymethyl-2-methyl-3-(2-thenoyloxy)pyridine

To a solution of 0.9 g of 3-hydroxy-5-hydroxymethyl-2-methylpyridine hydrochloride in 5 ml. of pyridine was added dropwise 0.7 g. of 2-thenoyl chloride under cooling. The resulting mixture was stirred overnight, poured into ice-water and then extracted with chloroform. The extract was washed with water, dried over anhydrous sodium sulfate and the solvent was distilled off to give an oily substance. This substance was purified by silica gel chromatography to give 0.75 g. of the desired product. m.p. 59° – 61°C.

Analysis for $C_{12}H_{11}NO_3S$ Calculated: C, 57.90; H, 4.46; N, 5.64; S, 12.84 Found: C, 57.74; H, 4.28; N, 5.88; S, 12.72.

IR spectrum (Nujol Mull) (cm$^{-1}$) $\sqrt{O}H$ 3180, $\sqrt{C}=O$ 1730.

REFERENTIAL EXAMPLE 2

5-Hydroxymethyl-3-isonicotinoyloxy-2-methylpiperidine

To a solution of 0.9 g. of 3-hydroxy-5-hydroxymethyl-2-methylpiperidine hydrochloride in 10 ml. of pyridine was added to a solution of 0.9 g. of isonicotinoyl chloride hydrochloride in 25 ml. of dimethylformamide under cooling. The resulting mixture was stirred at room temperature for 16 hours. Then, the reaction mixture was poured into ice-water and extracted with chloroform. The extracted was washed with water, dried and the solvent was distilled off to give a crystalline substance. The substance was recrystallized from a mixture of ethyl acetate and hexane to give 0.7 g. of the desired product. m. p. 126° – 128°C.

Analysis for $C_{13}H_{12}N_2O_3$ Calculated: C, 63,92; H, 4.95; N, 11.47 Found: C, 63.87; H, 5.07; N, 11.60.

IR spectrum (Nujol Mull) (cm$^{-1}$) $\sqrt{O}H$ 3200, $\sqrt{C}=O$ 1745.

Following the substantially same procedure as shown in the referential examples 1 and 2, the pyridine derivative as recited below was prepared: 3-(2-Furoyloxy)-5-hydroxymethyl-2-methylpyridine (NO.12)

Colorless oil

Analysis for $C_{12}H_{11}NO_4$ Calculated: C, 61.80; H, 4.75; N, 6.01 Found: C, 61.63; H, 4.93; N, 5.97.

IR spectrum (liquid, cm$^{-1}$) $\sqrt{O}H$ 3205, $\sqrt{C}=O$ 1742.

REFERENTIAL EXAMPLE 3

3'-(2-Thenoyloxy)-5-(2-thenoyloxymethyl)-2-methylpyridine

To a solution of 0.9 g. of 3-hydroxy-5-hydroxymethyl-2-methylpyridine hydrochloride in 7 ml. of pyridine was added dropwise 2.0 g. of 2-thenoyl chloride under cooling. The resulting mixture was stirred at room temperature for 16 hours. Then, the reaction mixture was poured into ice-water and extracted with chloroform. The extract was washed with water, dried over anhydrous sodium sulfate and the solvent was distilled off to give an oily substance. The substance was purified by silica gel chromatography to give 1.3 g. of the desired product. m. p. 72° – 74°C.

Analysis for $C_{17}H_{13}NO_4S_2$ Calculated: C, 54.68; H, 3.62; N, 3.90; S, 18.35 Found: C, 54.54; H, 3.47; N, 4.02; S, 18.19.

IR spectrum (Nujol Mull) (cm$^{-1}$) $\sqrt{C}=O$ 1725, 1715.

Following the above procedures were prepared the compounds as shown below. 2-Methyl-3-nicotinoyloxy-5-nicotinoyloxymethylpyridine, m. p. 97° – 98°C.

Analysis for $C_{19}H_{15}N_3O_4$ Calculated: C, 65.32; H, 4.33; N, 12.03 Found: C, 65.24; H, 4.31; N, 12.17

IR spectrum (Nujol Mull) (cm$^{-1}$) $\sqrt{C}=O$ 1730 3-(2-Furoyloxy)-5-(2-furoyloxymethyl)-2-methylpyridine (NO.6) m. p. 118° – 119°C.

Analysis for $C_{17}H_{13}NO_6$ Calculated: C, 62.38; H, 4.00; N, 4.28 Found: C, 62.75; H, 4.21; N, 4.14.

IR spectrum (Nujol Mull) (cm$^{-1}$) $\sqrt{C}=O$ 1740.

REFERENTIAL EXAMPLE 4

3-Hydroxy-5-isonicotinoyloxymethyl-2-methylpyridine

To a solution of 2.4 g. of 3-acetoxy-5-hydroxymethyl-2-methylpyridine hydrochloride in 20 ml. of pyridine was added a solution of 2.0 g. of isonicotinoyl chloride hydrochloride in 15 ml. of dimethylformamide under cooling and the resulting mixture was stirred at room temperature for 16 hours. Then, the reaction mixture was poured into ice-water and the mixture was extracted with chloroform. The extract was washed with water, dried over anhydrous sodium sulfate and the solvent was distilled off to give an oily substance. The substance was taken into 25 ml. of 2N HCl and the resulting mixture was stirred at 80°C. for 30 minutes. The mixture was neutralized with sodium bicarbonate, filtered and recrystallized from methanol to give 0.9 g. of the desired product. m. p. 180° – 180.5°C.

Analysis for $C_{13}H_{12}N_2O_3$ Calculated: C, 63.92; H, 4.95; N, 11.47 Found: C, 64.00; H, 5.00; N, 11.39.

IR spectrum (Nujol Mull) (cm$^{-1}$) $\sqrt{O}H$ 2475, $\sqrt{C}=O$ 1730.

The foregoing procedures were employed to prepare the two compounds shown below.

3-Hydroxy-2-methyl-5-nicotinoylxymethylpyridine, m. p. 211° – 213°C.

analysis for $C_{13}H_{12}N_2O_3$ Calculated: C, 63.92; H, 4.95; N, 11.47 Found: C, 64.00; H, 4.88; N, 11.51.

IR spectrum (Nujol Mull) (cm$^{-1}$) $\sqrt{C}=O$ 1715. 5-(2-Furoyloxymethyl)-2-methyl-3-pyridinol (NO.3) m. p. 192°C.

Analysis for $C_{12}H_{11}NO_4$ Calculated: C, 61.80; H, 4.75; N, 6.01 Found: C, 61.65; H, 4.58; N, 5.96.

IR spectrum (Nujol Mull) (cm$^{-1}$) $\sqrt{O}H$ 2500, $\sqrt{C}=O$ 1730.

REFERENTIAL EXAMPLE 5

3-Acetoxy-5-(2-furoyloxymethyl)-2-methylpyridine (NO.5)

To a solution of 1.1 g. of 3-acetoxy-5-hydroxymethyl-2-methylpyridine hydrochloride in 10 ml. of pyridine was added 0.75 g. of furoylchloride dropwise under cooling.

The mixture was stirred overnight at room temperature, then poured into ice-water and extracted with ethyl acetate. The extract was washed with water, dried and the solvent was distilled off to give an oily substance, which was purified by column chromatography (silica gel 30 g.) to give 1.5 g. of the desired product. Colorless oil.

Rf value of thin-layer chromatography: 0.76 (Plate, DC-Fertig platten Kieselgel available from Merck Co., Ltd., Developing solvent, ethyl acetate)

Analysis for $C_{14}H_{13}NO_5$ Calculated: C, 61.09; H, 4.76; N, 5.09 Found: C, 60,79; H, 4.52; N, 5.35.

The compounds of the formula (I) or the salts thereof are conveniently fed to poultry as a component of the feed or drinking water, but they may also be administered orally dispersed or admixed with other carriers.

According to one aspect of this invention, novel compositions are provided in which a pyridinol derivative or the salt thereof (I) is present as an active ingredient. Such compositions comprise the pyridinol derivative intimately dispersed in or admixed with an inert carrier. The term "inert carrier" as used herein means one that is substantially non-reactive with the active ingredient, orally ingestable and tolerated by the poultry.

The amount of pyridinol derivative required for control of coccidiosis in poultry will vary somewhat with the specific compound employed, the species of animals, the method or the object of application or with the symptoms. Generally, the pyridinol derivatives (I) are effective in preventing the disease without undesirable side effect and toxic effect when administered at a level of more than about 0.005 % by weight of the feed. For good prophylactic results, it is preferred that the feed contains between about 0.005 and 0.05 % by weight of the active ingredient, more preferably between about 0.01 and 0.015 %. When the pyridinol derivatives are to be employed for therapeutic purpose, the higher levels are used for a shorter period of time. Thus, the concentrations of about 0.1 % to about 0.2 % by weight of the feed may be advantageously administered for treatment of coccidiosis. When these compounds are to be employed for therapeutic purpose, it is desirable to employ the lowest levels that exhibit anticoccidial activities, in order to eliminate any risk of side effects that may appear on prolonged feeding.

In preparing solid compositions, an uniform dipersion of the active ingredient throughout the carrier can be readily accomplished by the conventional methods of grinding, stirring or milling.

Many of these pyridinol derivatives or the salts thereof are advantageously administered to poultry by way of the drinking water of the birds. This method of treatment may often be employed in the therapeutic use, since poultry with coccidiosis are apt to consume less solid feed than normal birds. The water-soluble quaternary salts may be added directly to the drinking water.

According to another aspect of this invention, novel compositions are provided in which an active ingredient is present in relatively large amounts and which are suitable for addition to the poultry feed directly or after an intermediate dilution step. Such compositions which are a preferred feature of this invention are the so-called feed supplements or premix. Representative examples of the carriers to be employed in this invention are solid oral carriers such as distillers dried grains, corn starch, potatoe starch, fermentation residues, ground oyster shells, Attapulgus clay, rice bran, wheat bran, wheat middling, molasses solubles, corn mean, edible vegetable substances, soybean cake, soybean meal, antibiotic mycelis, crushed lime stone and the like. The quaternary salts are intimately dispersed or admixed throughout the solid inert carriers as described hereinabove. Formulations containing from about 5% to about 30% by weight, of the active ingredient are particularly suitable for this purpose. It is preferable in the industry to use about 1 - 3 kg. of such a supplement per ton of feed.

Typical feed supplements containing pyridinol derivatives dispersed in an inert carrier include, for example, the following;

| | quaternary salt | parts by weight |
|---|---|---|
| A. | 5-hydroxymethyl-3-isonicotinoyl-oxy-2-methylpyridine | 25 |
| | wheat bran | 75 |

-continued

| | quaternary salt | parts by weight |
|---|---|---|
| B. | 2-methyl-5-isonicotinoyloxy-methyl-3-pyridinol | 20 |
| | rice bran | 80 |
| C. | 2-methyl-5-nicotinoyloxymethyl-3-pyridinol | 10 |
| | soybean meal | 90 |

According to another aspect of this invention, the present composition may preferably include other known anticoccidial agents to broaden its anticoccidial spectrum and, sometimes, expect a synergistic effect.

Suitable examples of such anticoccidial agents include, for example, sulfa drugs, e.g., Sulfachloropyrazine, Sulfadimethoxine, Sulfaquinoxaline; thiamine derivatives, e.g., Beclotiamine, Amprolium, Dimethialium; quinoline derivatives, e.g., Buquinolate, Decoquinate, Methyl Benzoquate; folic acid antagonistic substances, e.g., pyrimethamin, Diaveridine; antibiotics, e.g., Monensin; Zolene (3,5-dinitro-o-toluamide), Clopidol (3,5-dichloro-2,6-dimethyl-4-pyridinol), Robenzidine; and the like.

The formulation of the compounds and the coccidiostatic activety of the compounds are more fully illustrated by the non-limiting examples as follows.

In these examples, all the parts are given by weight unless otherwise indicated.

EXAMPLE 1

Fifteen parts of 5-hydroxymethyl-3-isonicotinoyloxy-2-methylpyridine are uniformly mixed with 85 parts of wheat bran.

The resulting feed supplement contains 15% active ingredient. Uniform mixing of one part of the supplement with 1,000 parts of the poultry feed gives a feed composition containing 0.015% active ingredient.

EXAMPLE 2

Five parts of 2-methyl-5-isonicotinoyloxy-3-pyridinol and 5 parts of Sulfachloropyradine are uniformly mixed with 90 parts of rice bran.

The resulting feed supplement contains 10% active ingredients in total. One part of the supplement is uniformly mixed with 10,000 parts of the poultry feed to give a feed containing 0.01% active ingredient in total.

EXAMPLE 3

The coccidiostatic activity of the pyridinol derivatives (I) or the salts thereof of this invention is determined by the following method:

Test Procedures

1. Chicks: Fourteen-day-old White Leghorn males (after being hatched, fed a diet containing no anticoccidial agent and isolated as far as possible from the risk of extraneous coccidial infections) were used.

Each group consisted of 10 chicks so as to avoid the difference of mean weight (significance level, 5%).

2. Infections: Each chicks was inoculated orally into the crop with 100,000 sporulated oocysts of Eimeria acervulina.

3. Concentration of tested compounds: Each tested compound was mixed to the commercially available mixed feed at a concentration of 200 ppm.

After inoculation with oocysts, the chicks are fed a diet containing tested compounds for 6 days.

Control groups of infected or non-infected chicks are fed a similar diet which is free from coccidiostat.

They are weighed from the beginning of the test to the end, constantly. Daily oocyst outputs are determined as oocysts per gram feces during a period from day 4 to 6. The daily samples from each treatment are pooled and recorded as a percentage to that of the infected-unmedicated control.

At the end of this time, that is, six days after infection all chicks are sacrificed and the degree of the lesion of small intestines are indicated as a 0 to 4 visual scale and determined by the method of Johnson and Reid described in Experimental Parasitology vol. 28, 30 – 36 pp., (1970).

4. Explanation of findings set forth in Table 1 and 2:

$$\text{Relative rate of weight gain (\%)} = \frac{\text{Average weight gain of each group}}{\text{Average weight gain of uninfected-unmedicated group}} \times 100$$

The total of the weight gain from the beginning of the test to the end divided with the number of the chicks is defined as "average weight gain".

$$\text{Rate of oocyst producton (\%)} = \frac{\text{Oocyst outputs of each}}{\text{Oocyst outputs of infected unmedicated group}} \times 100$$

The accumulated oocyst outputs per gram feces, during a period from day 4 to 6 is defined as "oocyst number".

$$\text{Mean lesion score of intestine} = \frac{\text{Total intestinal lesion of scores}}{\text{Number of chicks}}$$

The results are shown in Table 1.

Table 1

| Compound No. | Rate of oocyst production (%) | Relative rate of weight gain (%) | Mean lesion score of intestine |
|---|---|---|---|
| 1 | 0.2 | 95.4 | 0.4 |
| 3 | 1.4 | 88.5 | 1.4 |
| 4 | 1.4 | 94.7 | 0.2 |
| 6 | 0.5 | 93.5 | 1.0 |
| 7 | 6.8 | 92.3 | 1.2 |
| 9 | 9.1 | 89.2 | 1.6 |
| 10 | 0.8 | 92.7 | 0 |
| 11 | 0 | 98.0 | 0 |
| 12 | 0.8 | 93.9 | 0.4 |
| infected-unmedicated control | 100 | 60.1 | 4.0 |
| uninfected-unmedicated control | 0 | 100 | 0 |

It will be evident from the above results that the pyridinol derivatives of the abovementioned formula (I) or the salts thereof possess an extremely high degree of activity which cause coccidiosis, accompanying with good weight gain of the poultry without any unfavorable side effects.

What is claimed is:

1. An anticoccidial composition containing a minor amount, sufficient for the treatment of coccidiosis, which comprises a compound of the formula

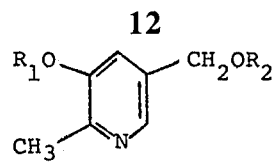

intimately dispersed in an inert edible carrier, wherein $R_1$ and $R_2$ are each hydrogen, an aliphatic acyl group, an aromatic acyl group or a heterocyclic acyl group selected from the group consisting of a furoyl group, a thenoyl group, a nicotinoyl group and an isonicotinoyl group, and at least $R_1$ or $R_2$ is said heterocyclic acyl group; or a salt thereof.

2. The anticoccidial composition of claim 1 wherein $R_1$ is a hydrogen atom and $R_2$ is a nicotinoyl group, an isonicotinoyl group, a furoyl group or a thenoyl group.

3. The anticoccidial composition of claim 1 wherein $R_1$ is a furoyl group, a thenoyl group, a nicotinoyl group or an isonicotinoyl group and $R_2$ is a hydrogen atom.

4. The anticoccidial composition of claim 1 wherein both $R_1$ and $R_2$ are the same and each represents a nicotinoyl group, an isonicotinoyl group, a furoyl group or a thenoyl group.

5. The composition of claim 1 wherein the compound is 5-hydroxymethyl-2-methyl-3-(2-thenoyloxy)-pyridine.

6. The composition of claim 1 wherein the compound is 5-hydroxymethyl-2-methyl-3-nicotinoyloxypyridine.

7. The composition of claim 1 wherein the compound is 5-(2-furoyloxymethyl)-2-methyl-3-pyridinol.

8. The composition of claim 1 wherein the compound is 2-methyl-5-nicotinoyloxymethyl-3-pyridinol.

9. The composition of claim 1 wherein the compound is 3-acetoxy-5-(2-furoyloxymethyl)-2-methylpyridine.

10. The composition of claim 1 wherein the compound is 3-(2-furoyloxy)-5-(2-furoyloxymethyl)-2-methylpiridine.

11. The composition of claim 1 wherein the compound is 2-methyl-3-nicotinoyloxy-5-nicotinoyloxymethylpyridine.

12. The composition of claim 1 wherein the compound is 3-benzoyloxy-5-(2-furoyloxymethyl)-2-methylpyridine.

13. The composition of claim 1 wherein the compound is 3-(2-thenoyloxy)-5-(2-thenoyloxymethyl)-2-methylpyridine.

14. The composition of claim 1 wherein the compound is 5-isonicotinoyloxymethyl-2-methyl-3-pyridinol.

15. The composition of claim 1 wherein the compound is 5-hydroxymethyl-3-isonicotinoyloxy-2-methylpyridine.

16. The composition of claim 1 wherein the compound is 3-(2-furoyloxy)-5-hydroxymethyl-2-methylpyridine.

17. The composition of claim 1 wherein the compound is 2-methyl-5-(2-thenoyloxymethyl)-3-pyridinol.

18. The composition of claim 1 wherein the compound is 3-acetoxy-5-(2-thenoyloxymethyl)-2-methylpyridine.

19. The composition of claim 1 wherein the compound is 3-acetoxy-2-methyl-5-nicotinoyloxymethylpyridine.

20. The composition of claim 1 wherein the compound is 3-acetoxy-5-isonicotinoyloxmethyl-2-methylpyridine.

21. The composition of claim 1 wherein the compound is 3-isonicotinoyloxy-5-isonicotinoyloxymethyl-2-methylpyridine.

22. A poultry feed having dispersed therein for control of poultry coccidiosis at least about 0.005% by weight of a compound of the formula

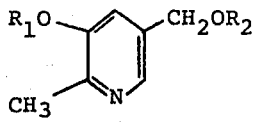

wherein $R_1$ and $R_2$ are each hydrogen, an aliphatic acyl group, an aromatic acyl group or a heterocyclic acyl group selected from the group consisting of a furoyl group, a thenoyl group, a nicotinoyl group and an isonicotinoyl group, and at least $R_1$ or $R_2$ is said heterocyclic acyl group; or a salt thereof.

23. The poultry feed of claim 2 wherein $R_1$ is hydrogen atom and $R_2$ is a nicotinoyl group, an isonicotinoyl group, a furoyl group or a thenoyl group.

24. The poultry feed of claim 22 wherein $R_1$ is a furoyl group, a thenoyl group, a nicotinoyl group or an isonicotinoyl group and $R_2$ is hydrogen atom.

25. The poultry feed of claim 22 wherein both $R_1$ and $R_2$ are the same and each represents a nicotinoyl group, an isonicotinoyl group, a furoyl group or a thenoyl group.

26. The poultry feed of claim 22 wherein the compound is 5-hydroxymethyl-2-methyl-3-(2-thenoyloxy)-pyridine.

27. The poultry feed of claim 22 wherein the compound is 5-hydroxymethyl-2-methyl-3-nicotinoyloxypyridine.

28. The poultry feed of claim 22 wherein the compound is 5-(2-furoyloxymethyl)-2-methyl-3-pyridinol.

29. The poultry feed of claim 22 wherein the compound is 2methyl-5-nicotinoyloxymethyl-3-pyridinol.

30. The poultry feed of claim 22 wherein the compound is 3-acetoxy-5-(2-furoyloxymethyl)-2-methylpyridine. pyridine.

31. The poultry feed of claim 22 wherein the compound is 3-(2-furoyloxy)-5-(2-furoyloxymethyl)-2-methylpyridine.

32. The poultry feed of claim 22 wherein the compound is 2-methyl-3-nicotinoyloxy-5-nicotinoyloxymethylpyridine.

33. The poultry feed of claim 22 wherein the compound is 3-benzoyloxy-5-(2-furoyloxymethyl)-2-methylpyridine.

34. The poultry feed of claim 22 wherein the compound is 3-(2-thenoyloxy)-5-(2-thenoyloxymethyl)-2-methylpyridine.

35. The poultry feed of claim 22 wherein the compound is 5-isonicotinoyloxymethyl-2-methyl-3-pyridinol.

36. The poultry feed of claim 22 wherein the compound is 5-hydroxymethyl-3-isonicotinoyloxy-2-methylpyridine.

37. The poultry feed of claim 22 wherein the compound is 3-(2-furoyloxy)-5-hydroxymethyl-2-methylpyridine.

38. The poultry feed of claim 22 wherein the compound is 2-methyl-5-(2-thenoyloxymethyl)-3-pyridinol.

39. The poultry feed of claim 22 wherein the compound is 3-acetoxy-5-(2-thenoyloxymethyl)-2-methylpyridine.

40. The poultry feed of claim 22 wherein the compound is 3-acetoxy-2-methyl-5-nicotinoyloxymethylpyridine.

41. The poultry feed of claim 22 wherein the compound is 3-acetoxy-5-isonicotinoyloxymethyl-2-methylpyridine.

42. The poultry feed of claim 22 wherein the compound is 3-isonicotinoyloxy-5-isonicotinoyloxymethyl-2methylpyridine.

43. A method of controlling poultry coccidiosis which comprises orally administering to poultry susceptible to coccidiosis an anticoccidial amount of a compound of the formula

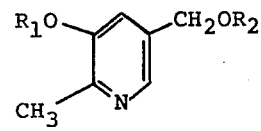

wherein $R_1$ and $R_2$ are each hydrogen, an aliphatic acyl group, an aromatic acyl group or a heterocyclic acyl group selected from the group consisting of a furoyl group, a thenoyl group, a nicotinoyl group and an isonicotinoyl group, and at least $R_1$ or $R_2$ is said heterocyclic acyl group; or a salt thereof.

44. The method of claim 43 wherein $R_1$ is a hydrogen atom and $R_2$ is a nicotinoyl group, an isonicotinoyl group, a furoyl group or a thenoyl group.

45. The method of claim 43 wherein $R_1$ is a furoyl group, a thenoyl group, a nicotinoyl group or an isonicotinoyl group and $R_2$ is hydrogen atom.

46. The method of claim 43 wherein both $R_1$ and $R_2$ are the same and each represents a nicotinoyl group, an isonicotinoyl group, a furoyl group or a thenoyl group.

47. The method of claim 43 wherein the compound is 5-hydroxymethyl-2-methyl-3-(2-thenoyloxy)pyridine.

48. The method of claim 43 wherein the compound is 5-hydroxymethyl-2-methyl-3-nicotinoyloxypyridine.

49. The method of claim 43 wherein the compound is 5-(2-furoyloxymethyl)-2-methyl-3-pyridinol.

50. The method of claim 43 wherein the compound is 2-methyl-5-nicotinoyloxymethyl-3-pyridinol.

51. The method of claim 43 wherein the compound is 3-acetoxy-5-(2-furoyloxymethyl)-2-methylpyridine.

52. The method of claim 43 wherein the compound is 3-(2-furoyloxy)-5-(2-furoyloxymethyl)-2-methylpyridine.

53. The method of claim 43 wherein the compound is 2-methyl-3-nicotinoyloxy-5-nicotinoyloxymethylpyridine.

54. The method of claim 43 wherein the compound is 3-benzoyloxy-5-(2-furoyloxymethyl)-2-methylpyridine.

55. The method of claim 43 wherein the compound is 3-(2-thenoyloxy)-5-(2-thenoyloxymethyl)-2-methylpyridine.

56. The method of claim 43 wherein the compound is 5-isonicotinoyloxymethyl-2-methyl-3-pyridinol.

57. The method of claim 43 wherein the compound is 5-hydroxymethyl-3-isonicotinoyloxy-2-methylpyridine.

58. The method of claim 43 wherein the compound is 3-(2-furoyloxy)-5-hydroxymethyl-2-methylpyridine.

59. The method of claim 43 wherein the compound is 2-methyl-5-(2-thenoyloxymethyl)-3-pyridinol.

60. The method of claim 43 wherein the compound is 3-acetoxy-5-(2-thenoyloxymetnyl)-2-methylpyridine.

61. The method of claim 43 wherein the compound is 3-acetoxy-2-methyl-5-nicotinoyloxymethylpyridine.

62. The method of claim 43 wherein the compound is 3-acetoxy-5-isonicotinoyloxymethyl-2-methylpyridine.

63. The method of claim 43 wherein the compound is 3-isonicotinoyloxy-5-isonicotinoyloxymethyl-2-methylpyridine.

64. A composition of claim 1 wherein said salt is an acid adduct salt of said compound and an acid selected from the group consisting of hydrochloric, sulfuric, nitric, phosphoric, acetic, propionic, lactic, oxalic, succinic, maleic, tartalic, citric, benzoic, phthalic, terephthalic and naphthalene sulfonic acid.

65. A poultry feed of claim 22 wherein said salt is an acid adduct salt of said compound and an acid selected from the group consisting of hydrochloric, sulfuric, nitric, phosphoric, acetic, propionic, lactic, oxalic, succinic, maleic, tartalic, citric, benzoic, phthalic, terephthalic and naphthalene sulfonic acid.

66. The method of claim 43 wherein said salt is an acid adduct salt of said compound and an acid selected from the group consisting of hydrochloric, sulfuric, nitric, phosphoric, acetic, propionic, lactic, oxalic, succinic, maleic, tartaric, citric, benzoic, phthalic, terephthalic and naphthalene sulfonic acid.

* * * * *

UNITED STATES PATENT OFFICE
CERTIFICATE OF CORRECTION

PATENT NO. : 3,983,238  Page 1 of 2
DATED : September 28, 1976
INVENTOR(S) : YASUHIRO MORISAWA et al It is certified that error appears in the above-identified patent and that said Letters Patent are hereby corrected as shown below:

Column 1, line 40: replace "cattles" with --- cattle ---.

Column 1, line 54: replace "of" (first occurrence) with --- or ---.

Column 4, line 38: rewrite "equilmoar" as --- equimolar ---

Column 7, line 17: replace "extracted" with --- extract ---.

Column 8, line 57: replace "60,79" with --- 60.79 ---.

Column 11, line 60 et seq.: in the fourt line of the paragraph beginning at line 60, delete the phrase "...activity which cause coccidiosis,..." and replace with --- ...activity against protozoa which cause coccidiosis,... ---.

UNITED STATES PATENT OFFICE
CERTIFICATE OF CORRECTION

PATENT NO. : 3,983,238
DATED : September 28, 1976
INVENTOR(S) : YASUHIRO MORISAWA et al It is certified that error appears in the above-identified patent and that said Letters Patent are hereby corrected as shown below:

Column 7, line 1: replace "($cm^{116\ 1}$)" with --- ($cm^{-1}$) ---.

Column 7, line 22: replace "63,92" with --- 63.92 ---.

Column 13, line 3 of Claim 30: delete "pyridine" (second occurrence).

Signed and Sealed this

Eleventh Day of October 1977

[SEAL]

Attest:

RUTH C. MASON
Attesting Officer

LUTRELLE F. PARKER
Acting Commissioner of Patents and Trademarks